US010857168B2

(12) United States Patent
McConnell et al.

(10) Patent No.: US 10,857,168 B2
(45) Date of Patent: Dec. 8, 2020

(54) SYNTHETIC COMPOSITION FOR MICROBIOTA MODULATION

(71) Applicant: Glycom A/S, Hørsholm (DK)

(72) Inventors: Bruce McConnell, La Tour de Peilz (CH); Louise Kristine Vigsnæs, Copenhagen (DK)

(73) Assignee: GLYCOM A/S, Hørsholm (DK)

( * ) Notice: Subject to any disclaimer, the term of this patent is extended or adjusted under 35 U.S.C. 154(b) by 0 days.

(21) Appl. No.: 16/079,959

(22) PCT Filed: Feb. 24, 2017

(86) PCT No.: PCT/DK2017/050046
§ 371 (c)(1),
(2) Date: Aug. 24, 2018

(87) PCT Pub. No.: WO2017/144062
PCT Pub. Date: Aug. 31, 2017

(65) Prior Publication Data
US 2019/0046546 A1 Feb. 14, 2019

(30) Foreign Application Priority Data

Feb. 24, 2016 (DK) .......................... PA 2016 70096

(51) Int. Cl.
| | | |
|---|---|---|
| *A61K 31/702* | (2006.01) | |
| *A61K 45/06* | (2006.01) | |
| *A61P 31/00* | (2006.01) | |
| *A61P 3/10* | (2006.01) | |
| *A61P 29/00* | (2006.01) | |
| *A61K 35/20* | (2006.01) | |
| *A61K 35/00* | (2006.01) | |

(52) U.S. Cl.
CPC ............ *A61K 31/702* (2013.01); *A61K 35/20* (2013.01); *A61K 45/06* (2013.01); *A61P 3/10* (2018.01); *A61P 29/00* (2018.01); *A61P 31/00* (2018.01); *A61K 35/00* (2013.01)

(58) Field of Classification Search
CPC ...... A61K 31/702; A61K 35/20; A61K 45/06; A61P 3/10; A61P 31/00; A61P 29/00
USPC .......................................................... 514/23
See application file for complete search history.

(56) References Cited

U.S. PATENT DOCUMENTS

| | | | |
|---|---|---|---|
| 2011/0158950 A1 | 6/2011 | Wacklin et al. | |
| 2012/0171165 A1* | 7/2012 | Buck .................. | A61K 31/702 514/23 |
| 2012/0294840 A1* | 11/2012 | Newburg ................ | C07H 3/06 424/93.44 |
| 2015/0087616 A1 | 3/2015 | Ritter et al. | |

FOREIGN PATENT DOCUMENTS

| | | |
|---|---|---|
| WO | 0104341 A1 | 1/2001 |
| WO | 2007101862 A1 | 9/2007 |
| WO | 2010115934 A1 | 8/2010 |
| WO | 2010015207 A1 | 9/2010 |
| WO | 2010115935 A1 | 10/2010 |
| WO | 2011100979 A1 | 8/2011 |
| WO | 2011100980 A1 | 8/2011 |
| WO | 2012007588 A9 | 1/2012 |
| WO | 2012113405 A1 | 8/2012 |
| WO | 2012127410 A1 | 9/2012 |
| WO | 2012155916 A1 | 11/2012 |
| WO | 2012156897 A1 | 11/2012 |
| WO | 2012156898 A1 | 11/2012 |
| WO | 2013044928 A1 | 4/2013 |
| WO | 2013091660 A1 | 6/2013 |
| WO | 2013139344 A1 | 9/2013 |
| WO | 2016066175 A1 | 5/2016 |
| WO | 2016091265 A1 | 6/2016 |

OTHER PUBLICATIONS

Wacklin et al. (PLoS ONE, May 2011 | vol. 6 | Issue 5 | e20113, 1-10).*
PCT/DK2017/050046, "Notification of Transmittal of the International Search Report and the Written Opinion of the International Searching Authority, or the Declaration", International Searching Authority, dated Nov. 5, 2017, pp. 1-23.
L. Peran et al., "A comparative study of the preventative effects exerted by three probiotics, Bifidobacterium lactis, Lactobacillus casei and Lactobacillus acidophilus, in the TNBS model of rat colitis", Journal of Applied Microbiology, pp. 1-9, ISSN 1364-5072.
Junjie Qin et al., "A human gut microbial gene catalogue established by metagenomic sequencing", nature, Mar. 4, 2010, pp. 1-9, vol. 464.
Kim-Anne Le et al., "Alterations in fecal Lactobacillus and Bifidobacterium species in type 2 diabetic patients in Southern China population", frontiers in Physiology, Jan. 31, 2013, pp. 1-6, doi: 10.3389.
Anna Ferrer-Admetlla et al., "A Natural History of FUT2 Polymorphism in Humans", The Author, Jun. 1, 2009, pp. 1-11, doi: 10.1093.
Min-Kyeong Cha et al., "Antiviral activity of Bifidobacterium adolescentis SPM1005-A on human papillomavirus type 16", BMC Medicine, 2012, pp. 1-6, 10:72.
Min Ji Kim et al., "Antiviral activity of Bifidobacterium adolescentis SPM1605 against Coxsackievirus B3", Biotechnology & Biotechnological Equipment, Feb. 28, 2014, pp. 681-688, vol. 28, No. 4.
Shinji Fukuda et al., "Bifidobacteria can protect from enteropathogenic infection through production of acetate", nature, Jan. 27, 2011, pp. 543-549, vol. 469.

(Continued)

*Primary Examiner* — Eric Olson
*Assistant Examiner* — Michael C Henry
(74) *Attorney, Agent, or Firm* — Kunzler Bean & Adamson

(57) ABSTRACT

This invention relates to a method and composition for modulating the microbiota in the gastro-intestinal tracts of non-infant humans who are carriers of the human fucosyltransferase 2 (FUT2) genetic mutation.

15 Claims, No Drawings

(56) References Cited

OTHER PUBLICATIONS

Maciej Chichlowski et al., "Bifidobacteria isolated from infants and cultured on human milk oligosaccharides affect intestinal epithelial function", National Institutes of Health, Sep. 1, 2013, pp. 1-17, doi: 10.1097.

Jiang Wu et al., "Bifidobacterium adolescentis Supplementation Ameliorates Parenteral Nutrition-Induced Liver Injury in Infant Rabbits", Springer, Jan. 22, 2010, pp. 2814-2820, doi:10.1007.

Jinjin Chen et al., "Bifidobacterium adolescentis supplementation ameliorates visceral fat accumulation and insulin sensitivity in an experimental model of the metabolic syndrome", British Journal of Nutrition, Sep. 14, 2011, pp. 1429-1434, doi: 10.1017.

Tae-Hwan Jung et al., "Butyrate modulates bacterial adherence on LS174T human colorectal cells by stimulating mucin secretion and MAPK signaling pathway", Nutrition Research and Practice, May 18, 2015, pp. 343-349.

C. Casen et al., "Deviations in human gut microbiota: a novel diagnostic test for determining dysbiosis in patients with IBS or IBD", AP&T Alimentary Pharmacology and Therapeutics, 2015, pp. 1-13.

Francesca Bottacini et al., "Diversity, ecology and intestinal function of bifidobacteria" Microbial Cell Factories, 2014, pp. 1-15.

Irene Fung et al., "Do Bugs Control Our Fate? The Influence of the Microbiome on Autoimmunity", Autoimmunity, Aug. 11, 2012, pp. 511-519, doi: 10.1007.

Marie Joossens et al., "Dysbiosis of the faecal microbiota in patients with Crohn's disease and their unaffected relatives", Gut, Jan. 5, 2011, pp. 1-8.

D. Guyonnet et al., "Effect of a fermented milk containing Bifidobacterium animalis DN-173 010 on the health-related quality of lift and symptoms in irritable bowel syndrome in adults in primary care: a multicentre, randomized, doubled-blind, controlled trial", Alimentary Pharmacology & Therapeutics, Apr. 30, 2007, pp. 1-12.

Christian Milani et al., "Evaluatino of bifidobacterial community composition in the human gut by means of a targeted amplicon sequencing (ITS) protocol", Federation of European Microbiological Societies, Sep. 8, 2014, pp. 1-11, doi: 10.1111.

Anna Klindworth et al., "Evaluatino of general 16S ribosomal RNA gene PCR primers for classical and next-generation sequencing-based diversity studies", Nucleic Acids Research, Aug. 28, 2012, pp. 1-11, vol. 41, No. 1.

Sabrina Duranti et al.,"Exploration of the Genomic Diversity and Core Genome of the Bifidobacterium adolescentis Phylogenetic Group by Means of a Polyphasic Approach", AEM, Jan. 2013, pp. 336-346, vol. 79, No. 1.

Dermot P.B. McGovern et al.,"Fucosyltransferase 2 (FUT2) non-secretor status is associated with Crohn's disease", Human Molecular Genetics, Jun. 2, 2010, pp. 3468-3476, vol. 19, No. 17.

Sabrina Duranti et al., "Genomic Characterization and Transcriptional Studies of the Starch-Utilizing Strain Bifidobacterium adolescentis 22L", AEM, Oct. 2014, pp. 6080-6090, vol. 80, No. 19.

Nadja Larsen et al., "Gut Microbiota in Human Adults with Type 2 Diabetes Differs from Non-Diabetic Adults", PLOS One, Feb. 5, 2010, pp. 1-10, vol. 5, Issue 2.

SH Duncan et al., "Human colonic microbiota associated with diet, obesity and weight loss", International Journal Obesity, Sep. 9, 2008, pp. 1720-1724, doi: 10.1038.

"Human gut microbes associated with obesity", NATURE, Dec. 28, 2006, pp. 1022-1023, vol. 444.

L. Bode, "Human milk oligosaccharides and their beneficial effects", Division of Neonatology and Division of Gastroenterology and Nutrition, 2013, pp. 515-531.

Mark J. Gnoth et al., "Human Milk Oligosaccharides Are Minimally Digested In Vitro", Research Institute of Child Nutrition, Aug. 31, 2000, pp. 3014-3020.

J.C. Brand Miller et al., "Human Milk Oligosaccharides Are Not Digested and Absorbed in the Small Intestine of Young Infants", Proceedings of the Nutrition Society of Australia, 1995, p. 44.

Meike B Engfer et al., "Human milk oligosaccharides are resistant to enzymatic hydrolysis in the upper gastrointestinal tract", The American Journal of Clinical Nutrition, 2000, pp. 1589-1596.

Xi Chen, "Human Milk Oligosaccharides (HMOS): Structure, Function, and Enzyme-Catalyzed Synthesis", Department of Chemistry, University of California, 2015, pp. 113-190, vol. 72, ISNN 0065-2318.

Lisa Lindesmith et al., "Human susceptibility and resistance to Norwalk virus infection", Nature Medicine, May 2003, pp. 548-553, vol. 9, No. 5.

Julia S. Frick et al., "Identificaion of Commensal Bacterial Strains That Modulate Yersinia enterocolitica and Dextran Sodium Sulfate-Induced Inflammatory Responses: Implications for the Development of Probiotics", Infection and Immunity, Jul. 2007, pp. 1-8, vol. 75, No. 7.

T. Pozo-Rubio et al., "Immunostimulatory effect of faecal Bifidobacterium species of breast-fed and formula-fed Infants in a peripheral blood mononuclear cell/Caco-2 co-culture system", British Journal of Nutrition, 2010, pp. 1216-1223, doi: 10.1017.

Patrice D. Cani et al., "Involvement of gut microbiota in the development of low-grade inflammation and type 2 diabetes associated with obesity", Gut Microbes, Jul./Aug. 2012, pp. 279-288.

Nicholas J Talley et al., "Irritable bowel syndrome: a little understood organic bowel disease?", The Lancet, Aug. 17, 2002, pp. 555-564, vol. 360.

Christine M. Carey et al., "Lactic acid bacteria and bifidobacteria attenuate the proinflammatory response in intestinal epithelial cells induced by *Salmonella enterica* serovar Typhimurium", NRC Research Press, Nov. 1, 2012, pp. 9-17.

Angele PM Kerckhoffs et at., "Lower Bifidobacteria counts in both duodenal mucosa-associated and fecal microbiota in irritable bowel syndrome patients", World Journal of Gastroenterology, Jun. 21, 2009, pp. 2887-2892, ISSN 1007-9327.

Steven R. Gill et al., "Metagenomic Analysis of the Human Distal Gut Microbiome", National Institutes of Health, Jun. 2, 2006, pp. 1355-1359, doi: 10.1126.

Andreas Schwiertz et al., "Microbiota and SCFA in Lean and Overweight Healthy Subjects", Obesity Journal, Jan. 2010, pp. 190-195, vol. 18, No. 1.

Eugenia Bezirtzoglou et al., "Microbiota profile in feces of breast- and formula-fed newborns by using fluroresence in situ hybridization (FISH)", Anaerobe, Apr. 8, 2011, pp. 478-482.

Tadasu Urashima et al,. "Milk Oligosaccharides", Nova Biomedical, 2011, pp. 1-99, ISBN: 978-1-61122-831-1.

Hereve M. Blottiere et al,. "Molecular analysis of the effect of short-chain fatty acids on intestinal cell proliferation", Proceedings of the Nutrition Society, 2003, pp. 101-106, doi:10.1079.

Maria Mylonaki et al,. "Molecular Characterization of Rectal Mucosa-associated Bacterial Flora in Inflammatory Bowel Disease", Inflamm Bowel Dis, May 2005, pp. 481-487, vol. 11, No. 5.

David A. Sela et al,. "Nursing our microbiota: molecular linkages between bifidobacteria and milk oligosaccharides", Trends in Microbiology, 2010, pp. 298-307.

Alexandra Wittmann et al., Plasmacytoid Dendritic Cells Are Crucial in Bifidobacterium adolescentis-Mediated Inhibition of Yersinia enterocolitica Infection, PLOS ONE, Aug. 2013, pp. 1-10, vol. 8, Issue 8.

Timothy Buie, "Potential Etiologic Factors of Microbiome Disruption in Autism", Clinical Therapeutics, Apr. 6, 2015, pp. 976-983, vol. 37, No. 5.

Orazio Gabrielli et al., "Preterm Milk Oligosaccharides During the First Month of Lactation", the American Academy of Pediatrics, Nov. 28, 2011, pp. e1520-e1533, doi:10.1542.

Akria Shimotoyodome et al., "Short chain fatty acids but not lactate or succinate stimulate mucus release in the rat colon", Comparative Biochemistry and Physiology Part A, Feb. 28, 2000, pp. 525-531.

Cyrille Hoarau et al., "Supernatant of Bifidobacterium breve induces dendritic cell maturation, activation, and survival through a Tol-like receptor 2 pathway", American Academy of Allergy, Asthma and Immunology, 2006, pp. 696-702, doi: 10.1016.

(56) References Cited

OTHER PUBLICATIONS

Alvaro Belenguer et al., "Two Routes of Metabolic Cross-Feeding between Bifidobacterium adolescentis and Butyrate-Producing Anaerobes from the Human Gut", Applied and Environmental Microbiology, May 2006, pp. 3593-3599, vol. 72, No. 5.
Aline Corado Gomes et al. "Gut microbiota, probiotics and diabetes", Nutrition Journal, vol. 21 No. 1, Dec. 1, 2014, pp. 1-13.
Pirjo Wacklin et al., "Secretor Genotype (FUT2 gene) Is Strongly Associates with the Composition of Bifdobacteria in the Human Intestine", PLOS One, vol. 6, No. 5, May 19, 2011, pp. 1-10.
EPO, "European Search Report", dated Jul. 10, 2019, pp. 1-5.
E. Elison et al., "Oral supplementation of healthy adults with 2!-O-fucosyllactose and lacto-N-neotetraose is well tolerated and shills the intestinal microbiota", British Journal of Nutrition, Aug. 22, 2016, pp. 1-13.
G. Gibson et al., "The International Scientific Association for Probiotics and Prebiotics (ISAPP) consensus statement on the definition and scope of prebiotics", Nature Reviews | Gastroenterology & Hepatology, vol. 14, Aug. 2017, pp. 491-502.
G.V. Copppa et al, "Oligosaccharides in 4 Different Milk Groups, Bifidobacteria, and Ruminococcus obeum", JPGN, vol. 53, No. 1, Jul. 2011, pp. 80-87.

\* cited by examiner

SYNTHETIC COMPOSITION FOR MICROBIOTA MODULATION

FIELD OF THE INVENTION

This invention relates to a method and composition for modulating the microbiota in the gastro-intestinal tracts of non-infant humans who are carriers of the human fucosyl-transferase 2 (FUT2) genetic mutation, particularly for increasing the abundance of *Bifidobacterium adolescentis* (*B. adolescentis*) and/or *Bifidobacterium pseudocatenulatum* (*B. pseudocatenulatum*) in the microbiota of these humans. An increased abundance of *B. adolescentis* and/or *B. pseudocatenulatum* can help to create a more benign intestinal microbial community which can beneficially modulate gut barrier function and inflammatory responses in the intestine.

BACKGROUND OF THE INVENTION

It has been estimated that the human intestine harbours $10^{13}$ to $10^{14}$ bacterial cells and the number of bacteria outnumbers the total number of cells in the body by a factor of 10 (Gill et al, *Science* 312, 1355 (2006)). The microbiota of the human intestine is a complex and very dynamic microbial ecosystem, which is considered to serve numerous important functions for its human host, including protection against pathogens, induction of immune regulatory functions, nutrient processing and metabolic functions (Tojo, *World J. Gastroenterol.* 20, 15163 (2014)). The intestinal microbiota consists of various populations, which are important to preserve human health, and recent research has been able to link imbalances in the intestinal bacterial population to both intestinal and extra-intestinal inflammatory diseases (Buie, *Clin. Ther.* 37, 976 (2015); Fung et al, *Curr. Allergy Asthma Rep.* 12, 511 (2012); Ley et al, *Nature* 444, 1022 (2006); Larsen et al, *PLoS One* 5, e9085 (2010)).

Selective stimulation of specific intestinal bacteria to promote their growth and metabolic activity could be a helpful approach in creating a benign intestinal microbial community.

Because some bacteria are able to produce a large selection of carbohydrate active enzymes (such as glycoside-hydrolases and transporters), the bacteria can grow on carbon sources, which may be less easily used by other members of the intestinal microbial community.

Human milk oligosaccharides (HMOs) are a heterogeneous mixture of soluble glycans found in human milk. They are the third most abundant solid component after lactose and lipids in human milk and are present in concentrations of 5-25 g/l (Bode: Human milk oligosaccharides and their beneficial effects. In: Handbook of dietary and nutritional aspects of human breast milk (Zibadi et al (eds.)) pp. 515-32. Wageningen Academic Publishers (2013); Gabrielli et al, *Pediatrics* 128, e1520 (2011)). HMOs are resistant to enzymatic hydrolysis in the small intestine and are thus largely undigested and unabsorbed (Gnoth et al, *J. Nutr.* 130, 3014 (2000); Engfer et al, *Am. J. Clin. Nutr.* 71, 1589 (2000); Brand-Miller et al, *P. Nutr. Soc. Australia* 19, 44 (1995)). The majority of HMOs that reach the colon serve as substrates to shape the gut ecosystem by selectively stimulating the growth of specific bacteria. HMOs are believed to substantially modulate the infant gut microbiota and play a decisive role in the differences in the microbiota of formula-fed and breast-fed infants. These differences include the predominance of *bifidobacterium* in the gut of breast-fed infants compared to a more diverse gut microbiota in formula-fed infants (Sela et al, *Trends Microbiol.* 18, 298 (2010); Bezirtzoglou et al, *Anaerobe* 17, 478 (2011)). This is viewed as beneficial for the infant because strains of *bifidobacterium* species are believed to have a positive effect on gut health (Chichlowski et al, *J. Pediatr. Gastroenterol. Nutr.* 55, 1 (2012); Fukuda et al, *Nature* 469, 543 (2011); Peran et al, *J. Appl. Microbiol.* 103, 836 (2007)). However, it is not known if HMOs can stimulate the growth of bifidobacteria in the intestines of older children or adults.

Bifidobacteria are considered one of the most beneficial probiotics, and strains of *B. adolescentis* have been widely studied for their effects against specific pathogens. The mechanisms behind the protecting effect include enhancement of the host's immune system and suppression of pathogenic gene expression. A study has recently shown that *B. adolescentis* can protect mice from infection by Yersinia enterocolitica by modulating the host intestinal immune system by increasing plasmacytoid dendritic cell and regulatory T-cell frequencies (Wttmann et al, *PLoS One* 8, e71338 (2013)). In line with this, an in vitro study has shown that *B. adolescentis* can attenuate pathogen-triggered inflammation by inhibiting IL-8 cell secretion induced by *Salmonella Typhimurium* DT104 (Carey et al, *Can. J. Microbiol.* 59, 9 (2013)). *B. adolescentis* has also been found to have antiviral activity through suppression of viral gene expression (Cha et al, *BMC Med.* 10:72 (2012); Kim et al, *Biotechnol. Biotechnol. Equip.* 28, 681 (2014)). Metabolic end products such as short chain fatty acids (acetate, propionate and butyrate), produced during carbohydrate fermentation, also contribute to intestinal functionality and probiotic attributes of bifidobacteria. It has previously been shown that acetate produced by bifidobacteria can enhance intestinal defence mediated by epithelial cells and thereby protect the host against assault (Fukuda et al, *Nature* 469, 543 (2011)). In addition, while bifidobacteria do not produce butyrate as an end product of fermentation, the importance of metabolic cross-feeding on acetate by butyrate-producing bacteria in the gut has been demonstrated (Belenguer et al, *Appl. Environ. Microbiol.* 72, 3593 (2006); Duncan et al, *Int. J. Obes.* 32, 1720 (2008)). Butyrate is the primary energy source for colonocytes and has been reported to regulate the physical and functional integrity of the normal colonic mucosa by altering mucin gene expression (Shimotoyodome et al, *Comp. Biochem. Physiol. A Mol. Integr. Physiol.* 125, 525 (2000); Blottière et al, Proc. Nutr. Soc. 62, 101 (2003)). The increase of mucin protein induced by butyrate, has recently shown to elevate adherence of *B. adolescentis*, which subsequently reduced the adherent ability of *E. coli* (Jung et al, *Nutr. Res. Pract.* 9, 343 (2015)).

Obesity, the major risk factor for type 2 diabetes, is associated with changes in gut microbiota composition. An altered gut microbiota has the potential to affect host metabolism and energy storage and to affect gut permeability, and as a consequence, increase plasma lipopolysaccharides (LPS) and give rise to metabolic endotoxemia and insulin resistance (Cani et al, *Gut Microbes* 3, 279 (2012)). Lower levels of bifidobacteria have previously been detected in obese versus lean and diabetic versus non-diabetic individuals (Duncan et al, *Int. J. Obes.* 32, 1720 (2008); Schwiertz et al, *Obesity* 18, 190 (2010)). *B. adolescentis* in particular has been observed to be underrepresented in type 2 diabetic patients compared to controls (Lê et al, *Front. Physiol.* 1 (2013)). Studies have shown that *B. adolescentis* can reduce intestinal permeability (Wu et al, Dig. Dis. Sci. 55, 2814 (2010)), and can ameliorate visceral fat accumulation and insulin sensitivity (Chen et al, *Br. J. Nutr.* 107, 1429 (2012)), hence inhibiting the pathological conditions of obesity.

The microbial composition has also been suggested to play a role in the pathophysiology of intestinal diseases such as IBD and IBS (Qin et al, *Nature* 464, 59 (2010); Talley et al, *Lancet* 360, 555 (2002)). Alterations in intestinal microbial composition in both IBD and IBS patients have been reported, and studies have revealed a lower number of bifidobacteria in both IBS and IBD compared to healthy subjects (Sokol et al, *Inflamm. Bowel Dis.* 15, 1183 (2009); Mylonaki et al, *Inflamm. Bowel Dis.* 11, 481 (2005); Kerckhoffs et al, *World J. Gastroenterol.* 15, 2887 (2009); Casén et al, *Aliment. Pharmacol. Ther.* 42, 71 (2015)). Dysbiosis has recently been established in IBD by characterization of five species including decreased abundance of *B. adolescentis* (Joossens M et al, *Gut* 60, 631 (2011)). Certain *bifidobacterium* species, including *B. adolescentis*, have been reported to provide benefits against conditions like IBD and IBS (Whorwell et al, *Am. J. Gastroenterol.* 101, 1581 (2006); Guyonnet et al, *Aliment. Pharmacol. Ther.* 26, 475 (2007); Chen et al, *World J. Gastroenterol.* 15, 321 (2009); Frick et al, *Infect. Immun.* 75, 3490 (2007)); one mode of action could be the immunomodulatory capacity of these species, acting as IL-10 inducer enhancing an anti-inflammatory immune response (Pozo-Rubio et al, *Br. J. Nutr.* 106, 1216 (2011); Hoarau et al, *J. Allergy Clin. Immunol.* 117, 696 (2006)).

The microbial composition of the intestine depends on multiple factors including diet and lifestyle, but genetic predisposition is increasingly recognised as an important factor. Among the genetic factors the FUT2 gene plays a central role (McGovern et al, *Hum. Mol. Genet.* 19, 3468 (2010)). The FUT2 gene encodes a fucosyl transferase enzyme that catalyses the attachment of a fucosyl moiety to the growing H Type-1 antigen, which is a key step in the assembly and subsequent secretion of ABO-antigens into mucosal layers (Lindesmith et al, *Nat. Med.* 9, 548 (2003)). The FUT2 gene exists in two basic forms; an active form (the "secretor" form) and an inactive form (the "non-secretor" form). Individuals who carry at least one copy of the secretor form secrete the ABO-antigens and display them on mucosal surfaces, including the mucosal lining of the gut. Individuals who carry only non-secretor versions of the FUT2 gene do not produce and secrete ABO-antigens and no ABO-antigens are found in the mucosal layers.

The effects of the FUT2 polymorphisms on gastro-intestinal health are thought to occur because the oligosaccharide structures of the ABO-antigen serve as attachment points for a number of microorganisms. The presence of the ABO-antigen appears to favour colonisation of the human digestive tract by beneficial bacteria and, as a consequence, reduces the risk of excessive inflammatory responses. In this context the secretor form of the FUT2 gene has a protective function and individuals who carry at least one copy of the secretor version of FUT2 are less likely to develop problems involving impaired gut barrier function and inflammatory responses. Humans carrying the non-secretor form of the FUT2 gene have much reduced abundance of bifidobacteria including *B. adolescentis* and/or *B. pseudocatenulatum*.

Therefore, it would be beneficial to preferentially increase the abundance, particularly the relative abundance, of bifidobacteria, in particular a *Bifidobacterium* of the *B. adolescentis* phylogenetic group, especially *B. adolescentis* and/or *B. pseudocatenulatum*, in the microbiota in the gastro-intestinal tracts of humans carrying FUT2 genetic mutation. However, it is unclear how to effectively increase the abundance, particularly the relative abundance, of a *Bifidobacterium* of the *B. adolescentis* phylogenetic group, especially *B. adolescentis* and/or *B. pseudocatenulatum*, in human microbiota. Genomic analyses of strains of *B. adolescentis* indicate that *B. adolescentis* has a nutrient acquisition strategy targeting plant-derived glycans, in particular starch and starch-like carbohydrates (Duranti et al, *Appl. Environ. Microbiol.* 80, 6080 (2014)). This fits with its increased abundance in older children and adolescence as the diet increasingly includes starches. However, many organisms in the gastro-intestinal tract target plant-derived glycans such as starch. Hence, feeding starches will not preferentially increase the abundance of *B. adolescentis* and/or *B. pseudocatenulatum* but rather will increase all the organisms able to metabolise starch. It may also be possible to administer *B. adolescentis* and/or *B. pseudocatenulatum* strains as probiotics. However, the long term viability of *B. adolescentis* and/or *B. pseudocatenulatum* strains in the gastro-intestinal tract is unclear. In in vitro tests, *B. adolescentis* generally shows no ability to grow in breast milk and utilise human milk oligosaccharides (Wittmann et al, *PLoS One* 8, e71338 (2013)); unlike *B. infantis, B. bifidum* and *B. breve* species. This is corroborated by the relative absence of *B. adolescentis* in the infant intestinal tract.

WO 2011/080395 discloses a probiotic composition comprising bifidobacterial strains which is tailored based on the bifidobacteria found in the intestine of an individual with non-secretor blood group phenotype, that is having no functional FUT2 gene.

There is a need, therefore, for means, preferably orally or enterally administered means, more preferably dietetic means, for effectively increasing the abundance, particularly the relative abundance of bifidobacteria, in particular a *Bifidobacterium* of the *B. adolescentis* phylogenetic group, especially *B. adolescentis* and/or, in the microbiota of the gastro-intestinal tracts of humans, preferably non-infant humans, carrying a FUT2 genetic mutation.

SUMMARY OF THE INVENTION

A first aspect of this invention relates to a fucosylated HMO for use in increasing the abundance, particularly the relative abundance, of bifidobacteria, in particular a *Bifidobacterium* of the *B. adolescentis* phylogenetic group, preferably *B. adolescentis* and/or *B. pseudocatenulatum*, in the microbiota in the gastro-intestinal tract of a human carrying a FUT2 genetic mutation. Preferably, the fucosylated HMO is for use in increasing the abundance of bifidobacteria, in particular a *Bifidobacterium* of the *B. adolescentis* phylogenetic group, preferably *B. adolescentis* and/or *B. pseudocatenulatum*, in the gastro-intestinal tract of a human, preferably a non-infant human, carrying a FUT2 genetic mutation in order to treat, to prevent in the human or to prevent the development in a human of:

an enteropathogenic infection,
type 2 diabetes,
impaired gut barrier function, and/or
an inflammation related to a gastro-intestinal condition.

In one embodiment, the fucosylated HMO is 2'-FL, 3-FL, DFL or LNFP-I, or a mixture thereof. In another embodiment, to the fucosylated HMO or a mixture or fucosylated HMOs can also be added a non-fucosylated HMO, for example a neutral HMO such as LNnT or LNT, or a mixture thereof. For example, the mixture can consist of a fucosylated HMO and a non-fucosylated neutral HMO.

A second aspect of this invention relates to a synthetic composition comprising a fucosylated HMO for use in increasing the abundance, particularly the relative abundance, of bifidobacteria, in particular a *Bifidobacterium* of the *B. adolescentis* phylogenetic group, preferably *B. adolescentis* and/or *B. pseudocatenulatum*, in the microbiota in the gastro-intestinal tract of a human carrying a FUT2 genetic mutation. Preferably, the synthetic composition is for use in increasing the abundance of bifidobacteria, in particular a *Bifidobacterium* of the *B. adolescentis* phylogenetic group, preferably *B. adolescentis* and/or *B. pseudocatenulatum*, in the gastro-intestinal tract of a human, preferably a non-infant human, carrying a FUT2 genetic mutation in order to treat, to prevent in the human or to prevent the development in a human of:

an enteropathogenic infection,
type 2 diabetes,
impaired gut barrier function, and/or
an inflammation related to a gastro-intestinal condition.

More preferably, the fucosylated HMO in the synthetic composition is 2'-FL, 3-FL, DFL or LNFP-1, or a mixture thereof. The composition can also include a non-fucosylated HMO, for example a neutral HMO such as LNnT or LNT, or a mixture thereof. For example, the composition can comprise a mixture of a fucosylated HMO and a non-fucosylated neutral HMO.

The synthetic composition can be a nutritional or pharmaceutical composition.

A third aspect of this invention is a method for increasing the abundance, particularly the relative abundance, of bifidobacteria, in particular a *Bifidobacterium* of the *B. adolescentis* phylogenetic group, especially *B. adolescentis* and/or *B. pseudocatenulatum*, in the microbiota in the gastro-intestinal tract of a human, preferably a non-infant human, carrying a FUT2 genetic mutation, the method comprising orally or enterally administering to the human an effective amount of a fucosylated human milk oligosaccharide.

A fourth aspect of this invention is a method for the prophylaxis or treatment of an enteropathogenic infection in a human, preferably a non-infant human, carrying a FUT2 genetic mutation, the method comprising orally or enterally administering, to the human, an amount of one or more fucosylated human milk oligosaccharides, effective to preferentially increase the abundance, particularly the relative abundance, of bifidobacteria, in particular a *Bifidobacterium* of the *B. adolescentis* phylogenetic group, especially *B. adolescentis* and/or *B. pseudocatenulatum*, in the microbiota in the gastro-intestinal tract of the human.

A fifth aspect of this invention is a method for the prophylaxis or treatment of a human, preferably a non-infant human, carrying a FUT2 genetic mutation and at risk of or having type 2 diabetes, the method comprising orally or enterally administering, to the human, an amount of one or more fucosylated human milk oligosaccharides, effective to preferentially increase the abundance, particularly the relative abundance, of bifidobacteria, in particular a *Bifidobacterium* of the *B. adolescentis* phylogenetic group, especially *B. adolescentis* and/or *B. pseudocatenulatum*, in the microbiota in the gastro-intestinal tract of the human. Preferably, the amount is effective to preferentially increase the abundance of bifidobacteria sufficiently to improve intestinal permeability and/or increase insulin sensitivity.

A sixth aspect of this invention is a method for the prophylaxis or treatment of a human, preferably a non-infant human, carrying a FUT2 genetic mutation and at risk of or having an inflammation related gastro-intestinal condition, the method comprising orally or enterally administering, to the human, preferably a non-infant human, an amount of one or more fucosylated human milk oligosaccharides, effective to preferentially increase the abundance, particularly the relative abundance, of bifidobacteria, in particular a *Bifidobacterium* of the *B. adolescentis* phylogenetic group, especially *B. adolescentis* and/or *B. pseudocatenulatum*, in the microbiota in the gastro-intestinal tract of the human. The gastro-intestinal condition may be intestinal bowel disease, irritable bowel syndrome or coeliac disease. Preferably, the amount is effective to preferentially increase the abundance of bifidobacteria sufficiently to induce an anti-inflammatory immune response.

A seventh aspect of this invention is a method for the prophylaxis or treatment of a human, preferably a non-infant human, carrying a FUT2 genetic mutation and at risk of or having an impaired gut barrier, the method comprising orally or enterally administering, to the human, an amount of one or more fucosylated human milk oligosaccharides, effective to preferentially increase the abundance, particularly the relative abundance, of bifidobacteria, in particular a *Bifidobacterium* of the *B. adolescentis* phylogenetic group, especially *B. adolescentis* and/or *B. pseudocatenulatum*, in the microbiota in the gastro-intestinal tract of the human. The human may be at risk of or have an intestinal bowel disease, irritable bowel syndrome, coeliac disease, obesity and or diabetes. Preferably, the amount is effective to preferentially increase the abundance of bifidobacteria sufficiently to repair the gut barrier permeability.

Concerning any of the aspects disclosed herein, the human is preferably a non-infant human and the bifidobacteria the abundance of which is to be increased is in particular a *Bifidobacterium* of the *B. adolescentis* phylogenetic group, especially *B. adolescentis* and/or *B. pseudocatenulatum*.

DETAILED DESCRIPTION OF THE INVENTION

It has now been surprisingly found by the present inventors that administration of fucosylated human milk oligosaccharides to humans, preferably non-infant children and adults, carrying a FUT2 genetic mutation preferentially increases the abundance of bifidobacteria, in particular a *Bifidobacterium* of the *B. adolescentis* phylogenetic group, especially *B. adolescentis* and/or *B. pseudocatenulatum*, in the microbiota of their gastro-intestinal tract.

Thus it has been discovered that fucosylated human milk oligosaccharides can, by oral or enteral ingestion, modulate the human intestinal microbiota by preferentially promoting the growth a *Bifidobacterium* of the *B. adolescentis* phylogenetic group, especially *B. adolescentis* and/or *B. pseudocatenulatum*, and increase the abundance of this/these species in the intestines of humans carrying a FUT2 genetic mutation. As an outcome, a more benign intestinal microbial community can be shaped and maintained, and by the increased abundance of a *Bifidobacterium* of the *B. adolescentis* phylogenetic group, especially *B. adolescentis* and/or *B. pseudocatenulatum*, pathogenic infections can be inhibited and gut barrier function and inflammatory responses in the intestine can be beneficially modulated. Preferably, the abundance of a *Bifidobacterium* of the *B. adolescentis* phylogenetic group, especially *B. adolescentis* and/or *B. pseudocatenulatum*, can be increased in the intestines of non-infant children and adults carrying a FUT2 genetic mutation.

"A *Bifidobacterium* of the *B. adolescentis* phylogenetic group" is meant a bacterium selected from a group consisting of *Bifidobacterium* adolescentis, *Bifidobacterium* angulatum, *Bifidobacterium* catenulatum, *Bifidobacterium* pseudocatenulatum, *Bifidobacterium* kashiwanohense, *Bifidobacterium dentum* and *Bifidobacterium stercoris* (Duranti et al, *Appl. Environ. Microbiol.* 79, 336 (2013), Bottacini et al, *Microbial Cell Fact.* 13:S4 (2014)).

"FUT2 genetic mutation" means a genetic mutation which renders the FUT2 gene or the gene product non-functional and unable to produce functional fucosyl-transferase. The invention relates to individuals carrying a FUT2 mutation that may have either mFUT2/wFUT2 or mFUT2/mFUT2, wherein "mFUT2" designates a mutatated FUT2 gene and "wFUT2" wild type gene. By "mutation" is meant a single nucleotide polymorphism, a deletion, an insertion, or any other genetic aberration of the FUT2 gene. By "FUT2 gene" is meant the gene having Gene ID: 2524, also known under the names SE; Se2; sej; SEC2; B12QTL1. The mutation may be detected in the gene sequence in situ or in the products of the gene, such as an RNA or protein, by any known in the art technique in a biological sample, such as e.g. a sample of blood or saliva, obtained from a human subject, preferably a non-infant human subject. The mutation may be a single mutation, such as a single nucleotide polymorphism (SNP), or multiple mutations; both the same type (e.g. two or more different SNP) or different type (e.g. an SNP and deletion) mutations are contemplated.

"Non-infant human" or "non-infant" preferably means a human of 3 years of age and older. A non-infant human can be a child, a teenager, an adult or an elderly.

"Human milk oligosaccharide" or "HMO" preferably means a complex carbohydrate found in human breast milk (Urashima T et al: *Milk Oligosaccharides*. Nova Science Publisher (2011); Chen, *Adv. Carbohydr. Chem. Biochem.* 72, 113 (2015)). The HMOs have a core structure comprising a lactose unit at the reducing end that can be elongated by one or more β-N-acetyl-lactosaminyl and/or one or β-more lacto-N-biosyl units, and which core structure can be substituted by an a L-fucopyranosyl and/or an α-N-acetyl-neuraminyl (sialyl) moiety. In this regard, the non-acidic (or neutral) HMOs are devoid of a sialyl residue, and the acidic HMOs have at least one sialyl residue in their structure. The non-acidic (or neutral) HMOs can be fucosylated or non-fucosylated. Examples of such neutral non-fucosylated HMOs include lacto-N-tetraose (LNT), lacto-N-neotetraose (LNnT), lacto-N-neohexaose (LNnH), para-lacto-N-neohexaose (pLNnH), para-lacto-N-hexaose (pLNH) and lacto-N-hexaose (LNH). Examples of neutral fucosylated HMOs include 2'-fucosyllactose (2'-FL), lacto-N-fucopentaose I (LNFP-I), lacto-N-difucohexaose I (LNDFH-O), 3-fucosyllactose (3-FL), difucosyllactose (DFL), lacto-N-fucopentaose II (LNFP-II), lacto-N-fucopentaose III (LNFP-III), lacto-N-difucohexaose III (LNDFH-III), fucosyl-lacto-N-hexaose II (FLNH-II), lacto-N-fucopentaose V (LNFP-V), lacto-N-difucohexaose II (LNDFH-II), fucosyl-lacto-N-hexaose I (FLNH-I), fucosyl-para-lacto-N-hexaose I (FpLNH-I), fucosyl-para-lacto-N-neohexaose II (F-pLNnH II) and fucosyl-lacto-N-neohexaose (FLNnH). Examples of acidic HMOs include 3'-sialyllactose (3'-SL), 6'-sialyllactose (6'-SL), 3-fucosyl-3'-sialyllactose (FSL), LST a, fucosyl-LST a (FLST a), LST b, fucosyl-LST b (FLST b), LST c, fucosyl-LST c (FLST c), sialyl-LNH (SLNH), sialyl-lacto-N-hexaose (SLNH), sialyl-lacto-N-neohexaose I (SLNH-I), sialyl-lacto-N-neohexaose II (SLNH-II) and disialyl-lacto-N-tetraose (DSLNT).

The term "synthetic composition" designates a composition which is artificially prepared and preferably means a composition containing at least one compound that is produced ex vivo chemically and/or biologically, e.g. by means of chemical reaction, enzymatic reaction or recombinantly.

In some embodiments a synthetic composition of the invention may be, but preferably is not, identical with a naturally occurring composition. The synthetic composition of the invention typically comprises one or more compounds, advantageously HMOs, that are capable of preferentially increasing the abundance of bifidobacteria, in particular a *Bifidobacterium* of the *B. adolescentis* phylogenetic group, especially *B. adolescentis* and/or *B. pseudocatenulatum*, in the microbiota of the gastro-intestinal tract. In some embodiments the synthetic composition may comprise one or more compounds or components other than HMOs that may have an effect on bifidobacteria of a human subject microbiota in vivo, e.g. non-digestible oligosaccharides or prebiotics. Also in some embodiments, the synthetic compositions may comprise one or more nutritionally or pharmaceutically active components which do not affect adversely the efficacy of the above mentioned compounds. Some non-limiting embodiments of a synthetic composition of the invention are also described below.

"Microbiota", "microflora" and "microbiome" preferably mean a community of living microorganisms that typically inhabits a bodily organ or part, particularly the gastro-intestinal organs of non-infant humans. The most dominant members of the gastrointestinal microbiota include microorganisms of the phyla of Firmicutes, Bacteroidetes, Actinobacteria, Proteobacteria, Synergistetes, Verrucomicrobia, Fusobacteria, and Euryarchaeota; at genus level *Bacteroides, Faecalibacterium, Bifidobacterium, Roseburia, Alistipes, Collinsella, Blautia, Coprococcus, Ruminococcus, Eubacterium* and *Dorea*; at species level *Bacteroides uniformis, Alistipes putredinis, Parabacteroides merdae, Ruminococcus bromii Dorea longicatena, Bacteroides caccae, Bacteroides thetaiotaomicron, Eubacterium hallii, Ruminococcus torques, Faecalibacterium prausnitzii, Ruminococcus lactaris, Collinsella aerofaciens, Dorea formicigenerans, Bacteroides vulgatus* and *Roseburia intestinalis*. The gastrointestinal microbiota includes the mucosa-associated microbiota, which is located in or attached to the mucus layer covering the epithelium of the gastrointestinal tract, and luminal-associated microbiota, which is found in the lumen of the gastrointestinal tract.

The term "enteral administration" preferably means any conventional form for delivery of a composition to a non-infant that causes the deposition of the composition in the gastrointestinal tract (including the stomach). Methods of enteral administration include feeding through a naso-gastric tube or jujenum tube, oral, sublingual and rectal.

The term "oral administration" preferably means any conventional form for the delivery of a composition to a non-infant through the mouth. Accordingly, oral administration is a form of enteral administration.

The term "effective amount" preferably means an amount of a composition that provides an HMO in a sufficient amount to render a desired treatment outcome in a non-infant. An effective amount can be administered in one or more doses to achieve the desired treatment outcome.

The term "relative abundance of bifidobacteria" preferably means the abundance of bifidobacteria relative to other genus in the microbiota of the gastro-intestinal tract of non-infants.

The term "relative growth of bifidobacteria" preferably means the growth of bifidobacteria relative to other genus in the microbiota in the gastro-intestinal tract of non-infants.

The term "relative abundance of a *Bifidobacterium* of the *B. adolescentis* phylogenetic group" preferably means the abundance of a *Bifidobacterium* of the *B. adolescentis* phylogenetic group relative to other bifidobacteria in the microbiota of the gastro-intestinal tract of humans, preferably non-infants.

The term "relative abundance of *B. adolescentis* and/or *B. pseudocatenulatum*" preferably means the abundance of *B. adolescentis* and/or *B. pseudocatenulatum* relative to other bifidobacteria in the microbiota of the gastro-intestinal tract of humans, preferably non-infants.

The term "relative growth of a *Bifidobacterium* of the *B. adolescentis* phylogenetic group" preferably means the growth of a *Bifidobacterium* of the *B. adolescentis* phylogenetic group relative to other bifidobacteria in the microbiota in the gastro-intestinal tract of humans, preferably non-infants. The term "relative growth of *B. adolescentis* and/or *B. pseudocatenulatum*" preferably means the growth of *B. adolescentis* and/or *B. pseudocatenulatum* relative to other bifidobacteria in the microbiota in the gastro-intestinal tract of humans, preferably non-infants.

"Prophylaxis" means treatment given or action taken to prevent the onset of a disease or a pathological condition, including reducing risks or threats to health.

In accordance with this invention, it has been discovered that a fucosylated HMO can promote the growth, particularly the relative growth, of bifidobacteria, in particular a *Bifidobacterium* of the *B. adolescentis* phylogenetic group, especially *B. adolescentis* and/or *B. pseudocatenulatum*, in the microbiota in the gastro-intestinal tract of humans, preferably non-infants, carrying a FUT2 genetic mutation. For this reason, a fucosylated HMO can be used for increasing the abundance, particularly the relative abundance, of bifidobacteria, in particular a *Bifidobacterium* of the *B. adolescentis* phylogenetic group, especially *B. adolescentis* and/or *B. pseudocatenulatum*, in the microbiota in the gastro-intestinal tract of humans, preferably non-infants, carrying a FUT2 genetic mutation. As a result, an HMO can be used for treating or preventing viral and/or bacterial infections (especially enteropathogenic infections), and conditions associated with impaired gut barrier function and intestinal inflammation; for example IBS, IBD, coeliac disease, obesity and type 2 diabetes in humans, preferably non-infants.

Accordingly, the invention relates to a fucosylated HMO or a synthetic composition comprising a fucosylated HMO for use in increasing the abundance, particularly the relative abundance, of bifidobacteria, in particular a *Bifidobacterium* of the *B. adolescentis* phylogenetic group, especially *B. adolescentis* and/or *B. pseudocatenulatum*, in the microbiota in the gastro-intestinal tract of humans, preferably non-infants, carrying a FUT2 mutation, and thereby treating and/or preventing viral and/or bacterial infections (especially enteropathogenic infections), and conditions associated with impaired gut barrier function and intestinal inflammation; for example IBS, IBD, coeliac disease, obesity and type 2 diabetes.

In one embodiment, the fucosylated HMO can be in neat form (i.e. undiluted) or diluted prior to administration, e.g. with water. Preferably, the fucosylated HMO is selected from the list consisting of 2'-FL, 3-FL, DFL, LNFP-I, LNFP-II, LNFP-III, LNFP-V, LNDFH-I, LNDFH-II, LNDFH-III, FLNH-I, FLNH-II, FLNnH, FpLNH-I and F-pLNnH II, more preferably from the list consisting of 2'-FL, 3-FL and DFL. In another embodiment, the fucosylated HMO can be mixed with a non-fucosylated neutral HMO. In this regard, the mixture contains, preferably consists of, one or more fucosylated HMOs as disclosed above, and one or more non-fucosylated HMOs, preferably non-fucosylated neutral HMOs, e.g. those selected from the list consisting of LNT, LNnT, LNH, LNnH, pLNH and pLNnH. Especially, the mixture contains, preferably consists of, a fucosylated HMO selected from the list consisting of 2'-FL, 3-FL and DFL, and a non-fucosylated neutral HMO selected from the list consisting of LNT and LNnT, advantageously the mixture comprises, preferably consists of, 2'-FL and LNnT.

Yet in another embodiment, the fucosylated HMO, the mixture of more fucosylated HMOs or the mixture containing, preferably consisting of, one or more fucosylated HMOs and one or more non-fucosylated HMOs, as disclosed above, can be comprised in a synthetic composition.

The HMOs can be isolated or enriched by well-known processes from milk(s) secreted by mammals including, but not limited to human, bovine, ovine, porcine, or caprine species. The HMOs can also be produced by well-known processes using microbial fermentation, enzymatic processes, chemical synthesis, or combinations of these technologies. As examples, using chemistry, LNnT can be made as described in WO 2011/100980 and WO 2013/044928, LNT can be synthesized as described in WO 2012/155916 and WO 2013/044928, a mixture of LNT and LNnT can be made as described in WO 2013/091660, 2'-FL can be made as described in WO 2010/115934 and WO 2010/115935, 3-FL can be made as described in WO 2013/139344, 6'-SL and salts thereof can be made as described in WO 2010/100979, sialylated oligosaccharides can be made as described in WO 2012/113404 and mixtures of human milk oligosaccharides can be made as described in WO 2012/113405. As examples of enzymatic production, sialylated oligosaccharides can be made as described in WO 2012/007588, fucosylated oligosaccharides can be made as described in WO 2012/127410, and advantageously diversified blends of human milk oligosaccharides can be made as described in WO 2012/156897 and WO 2012/156898. With regard to biotechnological methods, WO 01/04341 and WO 2007/101862 describe how to make core human milk oligosaccharides optionally substituted by fucose or sialic acid using genetically modified *E. coli*.

The synthetic composition can be a pharmaceutical composition. The pharmaceutical composition can contain a pharmaceutically acceptable carrier, e.g. phosphate buffered saline solution, mixtures of ethanol in water, water and emulsions such as an oil/water or water/oil emulsion, as well as various wetting agents or excipients. The pharmaceutical composition can also contain other materials that do not produce an adverse, allergic or otherwise unwanted reaction when administered to non-infants. The carriers and other materials can include solvents, dispersants, coatings, absorption promoting agents, controlled release agents, and one or more inert excipients, such as starches, polyols, granulating agents, microcrystalline cellulose, diluents, lubricants, binders, and disintegrating agents. If desired, tablet dosages of the anti-infective compositions can be coated by standard aqueous or non-aqueous techniques.

The pharmaceutical compositions can be administered orally, e.g. as a tablet, capsule, or pellet containing a predetermined amount, or as a powder or granules containing a predetermined concentration or a gel, paste, solution, suspension, emulsion, syrup, bolus, electuary, or slurry, in an aqueous or non-aqueous liquid, containing a predetermined concentration. Orally administered compositions can include binders, lubricants, inert diluents, flavouring agents, and humectants. Orally administered compositions such as tablets can optionally be coated and can be formulated so as to provide sustained, delayed or controlled release of the mixture therein.

The pharmaceutical compositions can also be administered by rectal suppository, aerosol tube, naso-gastric tube or direct infusion into the GI tract or stomach.

The pharmaceutical compositions can also include therapeutic agents such as antiviral agents, antibiotics, probiotics, analgesics, and anti-inflammatory agents. The proper dosage of these compositions for a non-infant human can be determined in a conventional manner, based upon factors such immune status, body weight and age. In some cases, the dosage will be at a concentration similar to that found for the HMO in human breast milk. The required amount would generally be in the range from about 200 mg to about 20 g per day, in certain embodiments from about 300 mg to about 15 g per day, from about 400 mg to about 10 g per day, in certain embodiments from about 500 mg to about 10 g per day, in certain embodiments from about 1 g to about 10 g per day. Appropriate dose regimes can be determined by conventional methods.

The synthetic composition can also be a nutritional composition. It can contain sources of protein, lipids and/or digestible carbohydrates and can be in powdered or liquid forms. The composition can be designed to be the sole source of nutrition or a nutritional supplement.

Suitable protein sources include milk proteins, soy protein, rice protein, pea protein and oat protein, or mixtures thereof. Milk proteins can be in the form of milk protein concentrates, milk protein isolates, whey protein or casein, or mixtures of both. The protein can be whole protein or hydrolysed protein, either partially hydrolysed or extensively hydrolysed. Hydrolysed protein offers the advantage of easier digestion which can be important for non-infants with inflamed GI tracts. The protein can also be provided in the form of free amino acids. The protein can comprise about 5% to about 30% of the energy of the nutritional composition, normally about 10% to 20%.

The protein source can be a source of glutamine, threonine, cysteine, serine, proline, or a combination of these amino acids. The glutamine source can be a glutamine dipeptide and/or a glutamine enriched protein. Glutamine can be included due to the use of glutamine by enterocytes as an energy source. Threonine, serine and proline are important amino acids for the production of mucin. Mucin coats the GI tract and can improve mucosal healing. Cysteine is a major precursor of glutathione, which is key for the antioxidant defences of the body.

Suitable digestible carbohydrates include maltodextrin, hydrolysed or modified starch or corn starch, glucose polymers, corn syrup, corn syrup solids, high fructose corn syrup, rice-derived carbohydrates, pea-derived carbohydrates, potato-derived carbohydrates, tapioca, sucrose, glucose, fructose, sucrose, lactose, honey, sugar alcohols (e.g., maltitol, erythritol, sorbitol), or mixtures thereof. Preferably the composition is free from lactose. Generally digestible carbohydrates provide about 35% to about 55% of the energy of the nutritional composition. Preferably the nutritional composition is free from lactose. A particularly suitable digestible carbohydrate is a low dextrose equivalent (DE) maltodextrin.

Suitable lipids include medium chain triglycerides (MCT) and long chain triglycerides (LCT). Preferably the lipid is a mixture of MCTs and LCTs. For example, MCTs can comprise about 30% to about 70% by weight of the lipids, more specifically about 50% to about 60% by weight. MCTs offer the advantage of easier digestion which can be important for non-infants with inflamed GI tracts. Generally the lipids provide about 35% to about 50% of the energy of the nutritional composition. The lipids can contain essential fatty acids (omega-3 and omega-6 fatty acids). Preferably these polyunsaturated fatty acids provide less than about 30% of total energy of the lipid source. Decreasing the levels of these polyunsaturated fatty acids is believed to decrease sensitivity to peroxidation; which can be beneficial for non-infants having inflammatory conditions.

Suitable sources of long chain triglycerides are rapeseed oil, sunflower seed oil, palm oil, soy oil, milk fat, corn oil, high oleic oils, and soy lecithin. Fractionated coconut oils are a suitable source of medium chain triglycerides. The lipid profile of the nutritional composition is preferably designed to have a polyunsaturated fatty acid omega-6 (n-6) to omega-3 (n-3) ratio of about 4:1 to about 10:1. For example, the n-6 to n-3 fatty acid ratio can be about 6:1 to about 9:1.

The nutritional composition preferably also includes vitamins and minerals. If the nutritional composition is intended to be a sole source of nutrition, it preferably includes a complete vitamin and mineral profile. Examples of vitamins include vitamins A, B-complex (such as B1, B2, B6 and B12), C, D, E and K, niacin and acid vitamins such as pantothenic acid, folic acid and biotin. Examples of minerals include calcium, iron, zinc, magnesium, iodine, copper, phosphorus, manganese, potassium, chromium, molybdenum, selenium, nickel, tin, silicon, vanadium and boron.

The nutritional composition can also include a carotenoid such as lutein, lycopene, zeaxanthin, and beta-carotene. The total amount of carotenoid included can vary from about 0.001 µg/ml to about 10 µg/ml. Lutein can be included in an amount of from about 0.001 µg/ml to about 10 µg/ml, preferably from about 0.044 µg/ml to about 5 g/ml of lutein. Lycopene can be included in an amount from about 0.001 µg/ml to about 10 µg/ml, preferably about 0.0185 mg/ml to about 5 g/ml of lycopene. Beta-carotene can comprise from about 0.001 µg/ml to about 10 mg/ml, for example about 0.034 µg/ml to about 5 µg/ml of beta-carotene.

The nutritional composition preferably also contains reduced concentrations of sodium; for example from about 300 mg/l to about 400 mg/l. The remaining electrolytes can be present in concentrations set to meet needs without providing an undue renal solute burden on kidney function. For example, potassium is preferably present in a range of about 1180 to about 1300 mg/l; and chloride is preferably present in a range of about 680 to about 800 mg/l.

The nutritional composition can also contain various other conventional ingredients such as preservatives, emulsifying agents, thickening agents, buffers, fibres and prebiotics (e.g. fructooligosaccharides, galactooligosaccharides), probiotics (e.g. *B. animalis* subsp. *lactis* BB-12, *B. lactis* HNO19, *B. lactis* Bi07, *B. infantis* ATCC 15697, *L. rhamnosus* GG, *L. rhamnosus* HNOOI, *L. acidophilus* LA-5, *L. acidophilus* NCFM, *L. fermentum* CECT5716, *B. longum* BB536, *B. longum* AH1205, *B. longum* AH1206, *B. breve* M-16V, *L. reuteri* ATCC 55730, *L. reuteri* ATCC PTA-6485, *L. reuteri* DSM 17938), antioxidant/anti-inflammatory compounds including tocopherols, caroteinoids, ascorbate/vitamin C, ascorbyl palmitate, polyphenols, glutathione, and superoxide dismutase (melon), other bioactive factors (e.g. growth hormones, cytokines, TFG-β), colorants, flavours, and stabilisers, lubricants, and so forth.

Suitable diluents, excipients, lubricants, colorants, binders, and disintegrants, for the purpose of making the synthetic composition, include polyethylene, polyvinyl chloride, ethyl cellulose, acrylate polymers and their copolymers, hydroxyethyl-cellulose, hydroxypropylmethyl-cellulose (H PMC), sodium carboxymethylcellulose, polyhydroxyethyl methylacrylate (PHEMA), polyvinyl alcohol (PVA), polyvinyl pyrrolidone (PVP), polyethylene oxide (PEO), or polyacrylamide (PA), carrageenan, sodium alginate, polycarbophil, polyacrylic acid, tragacanth, methyl cellulose, pectin, natural gums, xanthan gum, guar gum, karaya gum, hypromellose, magnesium stearate, microcrystalline cellulose, and colloidal silicon dioxide. Suitable antioxidants are vitamin A, carotenoids, vitamin C, vitamin E, selenium, flavonoids, polyphenols, lycopene, lutein, lignan, coenzyme Q10 ("CoQlO") and glutathione.

The nutritional composition can be in the form of a soluble powder, a liquid concentrate, or a ready-to-use formulation. The composition can be fed to a non-infant via a nasogastric tube or orally. Various flavours, fibres and other additives can also be present.

The nutritional compositions can be prepared by any commonly used manufacturing techniques for preparing nutritional compositions in solid or liquid form. For example, the composition can be prepared by combining various feed solutions. A protein-in-fat feed solution can be prepared by heating and mixing the lipid source and then adding an emulsifier (e.g. lecithin), fat soluble vitamins, and at least a portion of the protein source while heating and stirring. A carbohydrate feed solution is then prepared by adding minerals, trace and ultra trace minerals, thickening or suspending agents to water while heating and stirring. The resulting solution is held for 10 minutes with continued heat and agitation before adding carbohydrates (e.g. the HMOs and digestible carbohydrate sources). The resulting feed solutions are then blended together while heating and agitating and the pH adjusted to 6.6-7.0, after which the composition is subjected to high-temperature short-time processing during which the composition is heat treated, emulsified and homogenized, and then allowed to cool. Water soluble vitamins and ascorbic acid are added, the pH is adjusted to the desired range if necessary, flavours are added, and water is added to achieve the desired total solid level.

For a liquid product, the resulting solution can then be aseptically packed to form an aseptically packaged nutritional composition. In this form, the nutritional composition can be in ready-to-feed or concentrated liquid form. Alternatively, the composition can be spray-dried and processed and packaged as a reconstitutable powder.

When the nutritional product is a ready-to-feed nutritional liquid, the total concentration of HMOs in the liquid, by weight of the liquid, is from about 0.0001% to about 2.0%, including from about 0.001% to about 1.5%, including from about 0.01% to about 1.0%. When the nutritional product is a concentrated nutritional liquid, the total concentration of HMSs/HMOs in the liquid, by weight of the liquid, is from about 0.0002% to about 4.0%, including from about 0.002% to about 3.0%, including from about 0.02% to about 2.0%.

The synthetic composition can also be in a nutritional unit dosage form such as a capsule, tablet or sachet. For example, the synthetic composition can be in a tablet form comprising the HMOs, and one or more additional components to aid formulation and administration, such as diluents, excipients, antioxidants, lubricants, colorants, binders, disintegrants, and the like.

The unit dosage forms, especially those in sachet form, can also include various nutrients including macronutrients.

For increasing the abundance of bifidobacteria, in particular a *Bifidobacterium* of the *B. adolescentis* phylogenetic group, especially *B. adolescentis* and/or *B. pseudocatenulatum*, in the gastro-intestinal tract of a human, preferably a non-infant, carrying a FUT2 mutation, the amount of fucosylated HMO(s) required to be administered will vary depending upon factors such as the risk and severity of the medical condition, age, the form of the composition, and other medications being administered. However, the required amount can be readily set by a medical practitioner and would generally be in the range from about 10 mg to about 20 g per day, in certain embodiments from about 10 mg to about 15 g per day, from about 100 mg to about 10 g per day, in certain embodiments from about 500 mg to about 10 g per day, in certain embodiments from about 1 g to about 7.5 g per day. An appropriate dose can be determined based on several factors, including, for example, body weight and/or condition, the severity of the condition, being treated or prevented, other ailments and/or diseases, the incidence and/or severity of side effects and the manner of administration. Appropriate dose ranges may be determined by methods known to those skilled in the art. During an initial treatment phase, the dosing can be higher (for example 200 mg to 20 g per day, preferably 500 mg to 15 g per day, more preferably 1 g to 10 g per day, in certain embodiments 2.5 g to 7.5 g per day). During a maintenance phase, the dosing can be reduced (for example, 10 mg to 10 g per day, preferably 100 mg to 7.5 g per day, more preferably 500 mg to 5 g per day, in certain embodiments 1 g to 2.5 g per day).

Whilst the invention has been described with reference to a preferred embodiment, it is not limiting and various modifications are possible within the scope of the invention.

EXAMPLES

The working example described herein are for illustration purposes only and should not be considered as limiting.

Example 1

A total of 100 male and female healthy adults are recruited to participate in the study. After a screening visit and run-in period of 1-2 weeks, the participants are selected and randomized into ten groups, each of 10 subjects. One group is administered a placebo product containing 2 grams of glucose. The remaining 9 groups are administered treatment product containing a) 20 g of 2'-FL, b) 10 g of 2'-FL, c) 5 g of 2'-FL, d) 20 g of LNnT, e) 10 g of LNnT, f) 5 g of LNnT, g) 20 g of a 2:1 mixture of 2'-FL and LNnT, h) 10 g of a 2:1 mixture of 2'-FL and LNnT, and i) 5 g of a 2:1 mixture of 2'-FL and LNnT for 2 weeks (the amounts correspond to a daily dosis). The placebo and treatment products are in powder form in a unit dosage container.

The healthy adults are eligible to participate if they are at an age between 18-60 years. All recruited participants are able and willing to understand and comply with the study procedures. Participants are excluded if: they had participated in a clinical study one month prior to screening visit; they had abnormal results in the screening tests which were clinically relevant for study participation; they are suffering for a severe disease such as malignancy, diabetes, severe coronary disease, kidney disease, neurological disease, or severe psychiatric disease or any condition which could confound the results of the study; used highly dosed probiotic supplements (yoghurt allowed) for 3 months prior to the study; they consumed antibiotic drugs 6 months prior to the study; they consumed on a regular basis any medication that might have interfered with symptom evaluation 2 weeks prior to the study; and are pregnant or lactating.

At the screening visit, medical history and concomitant medication is registered and a blood sample for safety analyses is collected. A faecal sample kit is distributed. Participants are instructed to keep their samples in the freezer until the next visit.

At the second visit, eligibility criteria are checked and eligible subjects are randomised to the ten arms in the trial (treatment groups and placebo group). The faecal samples are collected and equipment for new samples are distributed. Participants are familiarised with an interactive internet enabled system which recorded data daily and are provided with either treatment or control products. Subjects are reminded not to change their usual diet during the study. Blood samples are collected for biomarker studies. The faecal samples are stored at −80° C. until analysis.

The study runs for 2 weeks with the participants consuming either a placebo or a treatment product daily. Participants are instructed to consume the products in the morning with breakfast. Compliance is monitored through the interactive internet enabled system.

The participants also use the system to record:
Bristol Stool Form Scale (BSFS) information.
Symptom information such as abdominal pain, abdominal discomfort, abdominal cramping, abdominal bloating, and abdominal fullness.
Additional, Gastrointestinal Symptom Rating Scale (GSRS) information.

This questionnaire includes 15 items covering five dimensions (abdominal pain, indigestion, reflux, diarrhoea, constipation) and uses a seven-graded Likert scale.

At the end of the study, each participant has an exit visit with the medical team. Faecal samples and blood samples are collected.

Blood samples are analysed simultaneously in a multiplexing format on an electrochemiluminescence platform. The following analytes are included in the panel: BUN, LDL cholesterol, HDL cholesterol, iron, triglycerides, ApoA1, ApoB, insulin, FFAs, glucagon, IL-10, IL-6 and TNF-α. The presence or absence of the mutation responsible for non-secretor genotype was determined by using sequencing method as described in the literature (Ferrer-Admetlla et al, *Mol. Biol. Evol.* 26, 1993 (2009)).

To assess the microbiota profile, DNA is extracted from the faecal samples using a 96-well PowerSoil DNA Isolation Kit (MO-BIO). A minimum of one sample-well per plate is kept empty to serve as a negative control during PCR. PCR is done with the forward primer S-D-Bact-0341-b-S-17 and reverse primer S-D-Bact-0785-a-A-21 (Klindworth et al, *Nucleic Acids Res.* 41, el (2013)) with Illumina adapters attached. These are universal bacterial 16S rDNA primers, which targeted the V3-V4 region. The following PCR program is used: 98° C. for 30 sec, 25× (98° C. for 10 s, 55° C. for 20 s, 72° C. for 20 s), 72° C. for 5 min. Amplification is verified by running the products on a 1% agarose gel. Barcodes are added in a nested PCR using the Nextera Index Kit V2 (Illumina) with the following PCR program: 98° C. for 30 sec, 8× (98° C. for 10 s, 55° C. for 20 s, 72° C. for 20 s), 72° C. for 5 min. Attachment of primers is verified by running the products on a 1% agarose gel. Products from the nested PCR are normalized using the SequalPrep Normalization Plate Kit and pooled. Pooled libraries are concentrated by evaporation and the DNA concentration of pooled libraries is measured on a Qubit fluorometer using the Qubit High Sensitivity Assay Kit (Thermo Fisher Scientific). Sequencing is done on a MiSeq desktop sequencer using the MiSeq Reagent Kit V3 (Illumina) for 2×300 bp paired-end sequencing. The 64-bit version of USEARCH is used for bioinformatical analysis of the sequence data.

The bifidobacteria abundance after consumption of HMOs as determined from faecal analyses increases for all treatment groups. The bifidobacteria abundance in healthy adults carrying the FUT2 mutation and receiving HMOs containing 2'-FL increases in a similar manner to that in FUT2 secretors.

To assess the *Bifidobacterium* community, ITS profiling of DNA samples is performed according to Milani et al. *FEMS Microbiol. Ecol.* 90, 493 (2014). Table 1 below shows the percentage increase of a *Bifidobacterium* species with high sequence similarity to *B. adolescentis* compared to that of other *Bifidobacterium* species identified in human faeces after consumption of HMOs as determined from faecal analyses. Additionally, the result from the profiling of the *Bifidobacterium* community shows that mainly the abundance of *B. adolescentis* increases when consuming a single HMO, whereas mainly the abundance of *B. pseudocatenulatum* increases when consuming a mix of two HMOs. Both *B. adolescentis* and *B. pseudocatenulatum* are members of the *B. adolescentis* phylogenetic group. It can be seen that oral ingestion of the HMOs clearly increases the abundance of *B. adolescentis* and/or *B. pseudocatenulatum* in the microbiota of healthy adults, as well as their relative abundance compared to the totality of other *Bifidobacterium* species.

TABLE 1

|  | *B. adolescentis* phylogenetic group | totality of *B. longum* + *B. bifidum* + *B. animalis lactis* + *B. angulatum* |
|---|---|---|
| 20 g LNnT | 185 | 105 |
| 10 g LNnT | 195 | 130 |
| 5 g LNnT | 90 | 50 |
| 20 g 2'-FL | 120 | 15 |
| 10 g 2'-FL | 325 | 20 |
| 5 g 2'-FL | 50 | 0 |
| 20 g mix | 320 | 265 |
| 10 g mix | 190 | 165 |
| 5 g mix | 25 | 20 |
| Placebo | 15 | −5 |

Further, the abundance of *B. adolescentis* and/or *B. pseudocatenulatum* in the microbiota of healthy adults carrying the FUT2 mutation and receiving 2'-FL, as well as the relative abundance compared to the totality of other *Bifidobacterium* species, increases in a manner similar to those in secretors.

Example 2

Thirty 12 weeks old Male C57bl6/J mice are individually housed to avoid contamination between mice. Prior to the experiment, the mice are randomly assigned to three groups, ten mice in each group. The mice are fed three different experimental diets for 14 weeks. Group one is fed a standard diet (control) (Altromin; no. 1324); group two is fed a high-fat diet containing 60% fat (Research diet; no. D12492); Group three is fed a mix of HF-diet containing 60% fat (Research diet; no. D12492) and 5% of HMO (2'-FL and LNnT, mass ratio 2:1). Fresh water is administered daily and all mice have free access to drinking water.

Fresh faecal samples are collected at day −5, 0, 14, 28, 56, 84, 98. Samples are immediately frozen and stored at −80° C. until further analysis.

Oral glucose tolerance tests are performed after 13 weeks of treatment in mice that are fasted for 6 h. Glucose is orally administered (3 g/kg body weight, 660 g/l glucose solution)

and blood glucose determined through a glucose meter using 3.5 µl of blood collected from the tip of the tail vein before and at administration of glucose load (−30 and 0 min) and after glucose load (15, 30, 60, 90 and 120 min). To assess plasma insulin concentration, 20 µl of blood is sampled 30 min before and 15 min following the glucose load.

Mice are euthanized by cervical dislocation after a 5 h period of fasting. Caecum (full and empty) and adipose tissues (epididymal, subcutaneous and visceral) are precisely dissected, weighed, immersed in liquid nitrogen and stored at −80° C., for further analysis.

Plasma LPS, cytokines and gut hormones are determined as follows. Plasma LPS concentration is measured using a kit based upon a Limulus amoebocyte extract (LAL kit endpoint-QCL1000). Samples are diluted ¹/₄₀ to ¹/₁₀₀ and heated for 20 cycles of 10 min at 68° C. and 10 min at 4° C. An internal control for LPS recovery is included in the calculation. Plasma cytokines (interleukin (IL) 1α, IL1b, tumour necrosis factor (TNF) α, IL6, monocyte chemoattractant protein (MCP)-1, macrophage inflammatory protein (MIP)-1α, IL10, interferon (INF) c, IL15, IL18) and gut hormones (GLP-1 (active), GIP (total), amylin (active), pancreatic polypeptide) are respectively determined in duplicate by using a Bio-Plex Multiplex kit, or a mouse gut hormones panel (LincoPlex), and measured by using Luminex technology, an EIA kit (GLP-2 EIA kit) is used to quantify GLP-2.

To determine the abundance of $B.$ adolescentis and/or $B.$ pseudocatenulatum, DNA is extracted from faecal samples and intestinal contents using QIAamp DNA Stool Mini Kit, and DNA concentration is measured using NanoDrop. The quantification of $B.$ adolescentis and/or $B.$ pseudocatenulatum is determined using quantitative PCR in a total reaction volume of 11 µl in 384-well microtiter plates using a LightCycler 480 II (Roche Applied Science). Each reaction will contain 1× SYBR green mix (Roche Applied Science), 0.2 pmol/µl of $B.$ adolescentis and/or $B.$ pseudocatenulatum specific primer (BiADO-1 ctc cag ttg gat gca tgt c/BiADO-2 cga agg ctt get ccc agt) and total bacteria primer (HDA1 act cct acg gga ggc agc agt/HDA2 gta tta ccg cgg ctg ctg gca c), and 2 µl template DNA (1 ng/µl). Reaction conditions are: 95° C. for 5 min, 40 cycles of 95° C. for 10 sec, 60° C. for 15 sec, and 72° C. for 45 sec, followed by melting curve generation (95° C. for 5 sec, 65° C. for 1 min and increasing the temperature to 98° C. with a rate of 0.11° C./sec with continuous fluorescence detection). Data is initially analysed in the LightCycler® 480 software. Noise band and threshold are set automatically using the LightCycler® 480 software. Cq-values are used for data analysis. The relative abundances of $B.$ adolescentis and/or $B.$ pseudocatenulatum normalized to the total number of 16S rRNA genes (total bacteria primer) are calculated.

To assess the microbiota profile, DNA is extracted from faecal samples and intestinal contents using QIAamp DNA Stool Mini Kit. The DNA concentration of extracts is measured using NanoDrop. The bacterial composition is determined by sequencing, as described in Example 1.

The results show that oral ingestion of HMOs modulate the intestinal microbiota, and increase the abundance of bifidobacteria, in particular a *bifidobacterium* of the $B.$ adolescentis phylogenetic group, especially $B.$ adolescentis and/or $B.$ pseudocatenulatum. Additionally, the results show that bifidobacteria of the $B.$ adolescentis phylogenetic group, especially $B.$ adolescentis and/or $B.$ pseudocatenulatum, negatively correlate with glucose intolerance, fasted insulinaemia, inflammatory markers, adipose tissue and body weight gain. Collectively, HMOs are able to increase bifidobacteria of the $B.$ adolescentis phylogenetic group, especially $B.$ adolescentis and/or $B.$ pseudocatenulatum, and by this, reduce endotoxaemia and improve glucose tolerance and insulin secretion, as well as reducing inflammation development in HF-diet-fed mice.

Example 3

A total of 60 male and female, adult IBS patients are recruited to participate in the study. After a screening visit and run-in period of 1-2 weeks, the patients are selected and randomised into 3 groups, each of 20 subjects. One group is administered a placebo product containing 5 grams of glucose. The remaining 2 groups are administered a treatment product containing a) 5 g of 4:1 mix of 2'-FL and LNnT, and b) 10 g of of 4:1 mix of 2'-FL and LNnT for 4 weeks. The placebo and treatment products are in powder form in a blinded unit dosage container.

The patients are eligible to participate if they are at an age between 18-60 years, fulfil the definition of IBS-D, IBS-C or IBS-A/M according to Rome IV criteria, and have a global IBS-SSS score of >174 during the 2 weeks run-in period. All recruited patients are able and willing to understand and comply with the study procedures. Patients are excluded if: they had participated in a clinical study one month prior to screening visit; they have gastrointestinal disease(s) which could interfere with the study outcome; they are suffering for a severe disease such as malignancy, diabetes, severe coronary disease, kidney disease, neurological disease, or severe psychiatric disease or any condition which could confound the results of the study; used highly dosed probiotic supplements (yoghurt allowed) for 1 month prior to the study; they consumed antibiotic drugs 1 month prior to the study; they consumed on a regular basis any medication that might have interfere with symptom evaluation 2 weeks prior to the study; were diagnosed with IBS more than 10 years prior to the study; and are pregnant or lactating.

At the first, screening visit, medical history and concomitant medication is registered and a blood sample for safety analyses is collected. IBS diagnostic criteria is assessed and part 1 of the IBS-SSS questionnaire is completed. A faecal sample kit is distributed. Participants are instructed to keep their samples in the freezer until the next visit.

At the second visit, eligibility criteria are checked and eligible subjects are randomised to the three arms in the trial (treatment groups and placebo group). The patients answer IBS symptom questionnaires (GSRS-IBS, IBS-SSS, HADS, NRS-11, VSI, IBS-QOL and PHQ-15 scales) and are characterised into one of the three following groups; diarrhoea predominant (IBS-D), constipation predominant (IBS-C) or alternating/mixed (IBS-A/M). A saliva sample is collected for analysis of FUT2 secretor status. Faecal samples are collected and equipment for new samples are distributed. Blood samples are collected for biomarker studies. The faecal samples are stored at −80° C. until analysis. Patients are provided with either treatment or control products sufficient for 4 weeks.

The study runs for 4 weeks with the participants consuming either a placebo or a treatment product daily.

At the third visit, the patients are physically examined. The patients answer IBS symptom questionnaires (GSRS-IBS, IBS-SSS, HADS, NRS-11, VSI, IBS-QOL and PHQ-15 scales. Remaining study products and compliance diaries are collected to check compliance. Faecal samples are collected and equipment for new samples are distributed. Blood samples are collected for biomarker studies. The faecal samples are stored at −80° C. until analysis.

The blood samples are analysed simultaneously in a multiplexing format on an electrochemiluminescence platform. The following analytes are included in the panel: cytokines, TH1, TH2, zonulin and lipopolysaccharide.

To assess the microbiota profile, DNA is extracted from the faecal samples using a 96-well PowerSoil DNA Isolation Kit (MO-BIO). A minimum of one sample-well per plate is kept empty to serve as a negative control during PCR. PCR is done with the forward primer S-D-Bact-0341-b-S-17 and reverse primer S-D-Bact-0785-a-A-21 (46) with Illumina adapters attached. These are universal bacterial 16S rDNA primers, which targeted the V3-V4 region.

The following PCR program is used: 98° C. for 30 sec, 25× (98° C. for 10 s, 55° C. for 20 s, 72° C. for 20 s), 72° C. for 5 min. Amplification is verified by running the products on a 1% agarose gel. Barcodes are added in a nested PCR using the Nextera Index Kit V2 (Illumina) with the following PCR program: 98° C. for 30 sec, 8× (98° C. for 10 s, 55° C. for 20 s, 72° C. for 20 s), 72° C. for 5 min. Attachment of primers is verified by running the products on a 1% agarose gel. Products from the nested PCR are normalized using the SequalPrep Normalization Plate Kit and pooled. Pooled libraries are concentrated by evaporation and the DNA concentration of pooled libraries is measured on a Qubit fluorometer using the Qubit High Sensitivity Assay Kit (Thermo Fisher Scientific). Sequencing is done on a MiSeq desktop sequencer using the MiSeq Reagent Kit V3 (Illumina) for 2×300 bp paired-end sequencing. The 64-bit version of USEARCH is used for bioinformatical analysis of the sequence data.

The saliva samples are analysed by Dynamic Code AB of Linkoping, Sweden for FUT2 status.

The bifidobacteria abundance after consumption of HMOs as determined from faecal analyses increases for all treatment groups. The bifidobacteria abundance in the patients carrying the FUT2 mutation and receiving treatment products increases in a similar manner to that in FUT2 secretors. The patients carrying the FUT2 mutation and receiving the control products remain at low bifidobacteria abundance.

The patients receiving the treatment products, including the patients carrying the FUT2 mutation, show improvement in IBS symptom scores.

The invention claimed is:

1. A method comprising:
    selecting a non-infant human carrying an FUT2 mutation associated with an FUT2 non-secretor status;
    selecting an effective amount of a product consisting essentially of one or more fucosylated neutral human milk oligosaccharides ("HMOs") selected from 2'-fucosyllactose (2'-FL), difucosyllactose (DFL), 3-fucosyllactose (3-FL), lacto-N-fucopentaose I (LNFP-I), and a mixture thereof, and optionally one or more non-fucosylated neutral HMOs selected from lacto-N-neotetraose (LNnT), lacto-N-tetraose (LNT), and a mixture thereof; and
    increasing the relative abundance of *Bifidobacterium adolescentis* in the gastrointestinal microbiota of the non-infant human relative to the abundance of other bifidobacteria by administering the effective amount of the product to the selected non-infant human.

2. The method of claim 1, further comprising improving in the non-infant human having the FUT2 mutation at least one condition selected from an enteropathogenic infection, an impaired gut barrier function, and an inflammation related to a gastrointestinal condition.

3. The method of claim 1, wherein the selected effective amount of the product consists essentially of one or more fucosylated neutral HMOs and one or more non-fucosylated neutral HMOs.

4. The method of claim 2, wherein:
    the selected non-infant human carrying the FUT2 mutation is an Irritable Bowel Syndrome ("IBS") patient; and
    the at least one condition improved by administering the effective amount of the product comprises an improved gut barrier function.

5. The method of claim 2, wherein the at least one condition improved by administering the effective amount of the product comprises reduction of the inflammation related to the gastrointestinal condition.

6. The method of claim 2, wherein the at least one condition improved by administering the effective amount of the product comprises reduction of the enteropathogenic infection.

7. A method comprising:
    selecting a non-infant human carrying an FUT2 mutation associated with an FUT2 non-secretor status and having a condition associated with an increased risk of developing obesity, type 2 diabetes, or both;
    selecting an effective amount of a product consisting essentially of one or more fucosylated neutral human milk oligosaccharides ("HMOs") selected from 2'-fucosyllactose (2'-FL), difucosyllactose (DFL), 3-fucosyllactose (3-FL), lacto-N-fucopentaose I (LNFP-I), and a mixture thereof, and optionally one or more non-fucosylated neutral HMOs selected from lacto-N-neotetraose (LNnT), lacto-N-tetraose (LNT), and a mixture thereof; and
    increasing the relative abundance of *Bifidobacterium adolescentis* in the microbiota in the gastro-intestinal tract of the non-infant human carrying the FUT2 mutation and improving in the non-infant human carrying the FUT2 mutation, the condition associated with the increased risk of developing obesity, type 2 diabetes, or both, by administering the effective amount of the product to the selected non-infant human.

8. The method of claim 7, wherein the improvement in the condition associated with the increased risk of developing obesity, type 2 diabetes, or both, is selected from reduced adipose tissue, reduced body weight gain, improved glucose tolerance, improved insulin secretion, and combinations thereof.

9. The method of claim 7, wherein the selected effective amount of the product consists essentially of one or more fucosylated neutral HMOs and one or more non-fucosylated neutral HMOs.

10. The method of claim 9, wherein the selected effective amount of the product consists essentially of
    a fucosylated neutral human milk oligosaccharide selected from 2'-FL, 3-FL, DFL, and a mixture thereof; and
    a non-fucosylated neutral human milk oligosaccharide selected from LNT, LNnT, and a mixture thereof.

11. A method comprising:
    selecting a non-infant human carrying an FUT2 mutation associated with an FUT2 non-secretor status;
    selecting an effective amount of a product consisting essentially of one or more synthetic neutral human milk oligosaccharides ("HMOs") selected from 2'-fucosyllactose (2'-FL), difucosyllactose (DFL), 3-fucosyllactose (3-FL), lacto-N-fucopentaose I (LNFP-I), and a mixture thereof, and optionally one or more non-fucosylated neutral HMOs selected from lacto-N-neotetraose (LNnT), lacto-N-tetraose (LNT), and a mixture thereof; and increase the relative growth of a *Bifidobacterium adolescentis* in the gastrointestinal microbiota of the non-infant human and improve in the non-infant human at least one condition selected from an enteropathogenic infection, an impaired gut barrier function, and an inflammation related to a gastrointestinal condition by administering the effective amount of the product to the selected non-infant human.

12. The method of claim 11, wherein the selected effective amount of the product consists essentially of one or more fucosylated neutral HMOs and one or more non-fucosylated neutral HMOs.

13. The method of claim 12, wherein the selected effective amount of the product consists essentially of one or more synthetic neutral HMOs selected from 2'-FL, LNnT, and a mixture of 2'-FL and LNnT.

14. The method of claim 13, wherein the selected effective amount of the product administered to the non-infant human is from about 2.5 g to about 10 g per day during an initial treatment phase.

15. The method of claim 14, wherein after completing the initial treatment phase, the selected effective amount of the product administered to the non-infant human is from about 500 mg to about 5 g per day during a maintenance phase.

* * * * *